(12) United States Patent
Courage

(10) Patent No.: US 6,619,423 B2
(45) Date of Patent: Sep. 16, 2003

(54) MEASURING DEVICE FOR MEASURING THE ELASTIC PROPERTIES OF A SURFACE STRUCTURE

(75) Inventor: Wilfried Courage, Cologne (DE)

(73) Assignee: Courage + Khazaka electronic GmbH, Koel (DE)

(*) Notice: Subject to any disclaimer, the term of this patent is extended or adjusted under 35 U.S.C. 154(b) by 0 days.

(21) Appl. No.: 09/885,110

(22) Filed: Jun. 21, 2001

(65) Prior Publication Data

US 2002/0029924 A1 Mar. 14, 2002

(30) Foreign Application Priority Data

Jun. 21, 2000 (EP) .............................. 00113235

(51) Int. Cl.⁷ ................................. G01V 1/00
(52) U.S. Cl. ................. 181/108; 181/101; 181/102; 181/103; 181/104; 181/105; 181/106; 181/107; 181/108; 181/109; 181/110; 181/111; 181/112; 73/597; 600/438
(58) Field of Search ................. 181/108, 101–112; 73/597; 600/438

(56) References Cited

U.S. PATENT DOCUMENTS 4,947,851 A * 8/1990 Sarvazyan et al. .......... 600/438
5,060,201 A * 10/1991 Ishikawa et al. ............. 367/7
5,335,208 A * 8/1994 Sansone ...................... 367/49

FOREIGN PATENT DOCUMENTS

EP 0 329 817 A2 6/1988

* cited by examiner

Primary Examiner—Bentsu Ro
Assistant Examiner—Renata McCloud
(74) Attorney, Agent, or Firm—Diller, Ramik & Wight

(57) ABSTRACT

A measuring device for measuring the elastic properties of a surface structure (3), comprising a probe (2) arranged within a housing (1), a transmitter and at least one receiver, the transmitter transmitting acoustic pulses and the receiver picking up the propagation behavior of the acoustic pulses in the surface structure (3), a control means (16) for generating acoustic pulses and an evaluating means (18) for the measuring signals received by the receiver, at least two adjacent measuring tips (4, 6) being connected as transmitting and receiving elements, the measuring tips being adapted to be set onto the surface structure (3) and having strip-shaped bi-morph elements (12, 14) carried by a holder (8, 10), wherein the measuring tips (4,6) are formed by the holders (8, 10) of the bi-morph elements (12, 14) and the strip-shaped elements (12, 14) have one side of one of their ends fastened to the holder (8, 10).

12 Claims, 2 Drawing Sheets

MEASURING DEVICE FOR MEASURING THE ELASTIC PROPERTIES OF A SURFACE STRUCTURE

BACKGROUND OF THE INVENTION

The present invention refers to a measuring device for measuring the elastic properties of a surface structure, as defined in the preamble of claim 1. Such a measuring device is known from EP 0 329 817. The known device comprises a probe supported for axial movement in a housing, the measuring tips of the probe being adapted to be orthogonally applied to the skin surface of a biological body, using a predefined contact pressure. The measuring tips transmit sound pulses from bi-morph piezo transducers into the skin surface, with one measuring tip acting as a transmitter and the other two acting as receivers. The receivers measure the time span between transmission and receipt of the acoustic pulse traveling through the skin between the measuring tips. From the time measured, the propagation velocity of the sound wave in the skin is calculated.

The flat and strip-shaped bi-morph piezo transducers consist of a ceramic material provided with electrodes and having low breaking strength. The bi-morph elements are thus very brittle and will break soon under mechanical stress.

It is the object of the present invention to provide a measuring device of the type mentioned above that has greater operational safety and is insensitive to impacts.

SUMMARY OF THE INVENTION

Advantageously, the invention provides that the measuring tips are formed by the holder for the bi-morph elements, the strip-shaped bi-morph elements being fixed to the holder only on one side and by one end. By making the holders of the bi-morph elements form the measuring tip themselves, the bi-morph elements are advantageously subjected to no mechanical stresses so that they will not break even when treated improperly or when subjected to high impact stresses.

Preferably, the bi-morph elements are fastened to the end of the holder facing the measuring tips. The holder allows for a transmission of acoustic pulses via the measuring tips onto the surface structure and simultaneously protects the bi-morph element against damage. The strip-shaped bi-morph elements are each fixed—preferably by glueing—to the holder at the free end thereof facing the surface structure, whereby an optimum transmission of the generated acoustic pulses onto the free end of the holder forming the measuring tip can be obtained.

At the respective free ends of each strip-shaped bi-morph element a seismic mass is fastened, preferably by glueing. When the bi-morph element of the transmitter deflects due to an electric pulse, the bending moment is transmitted as an acoustic pulse via the measuring tip onto the surface structure. This bending moment is supported by the seismic mass with its inertia. The inertia of the seismic mass causes a very sensitive reaction of the arrangement to fast pulses, yet hardly any reaction to the relatively slow movements caused by improper handling.

Preferably, the holders have a longitudinal recess adapted to the bi-morph elements in which the bi-morph elements can vibrate freely. The recesses allow the bi-morph elements extending parallel to the holders to vibrate through the recess when vibrating orthogonal to the holders.

The holders consist of two flat, strip-shapes members having their ends opposite the measuring tips fastened to a common support with a parallel distance therebetween. The holders are very flexible so that the acoustic pulses of the transmitter are not transmitted to the support. The preferred material for the holders is Makrolon. The flexibility of the holder inhibits transmission of the acoustic pulse onto the receiver via the suspension.

The probe is supported for axial movement in the housing and the measuring tips can be applied against the skin surface with a defined spring tension.

The acoustic pulse and the measurement can be triggered when the probe has traveled a predetermined path. This guarantees that the measuring tips are always pressed against the surface structure with the same contact pressure.

The acoustic pulse and the measurement may also be triggered after a predetermined time delay, which can also be combined with the signal's having traveling a certain probe path.

Preferably, the transmitter consisting of a flat bi-morph element couples a single acoustic pulse into the surface structure.

The measuring signals picked up by the receiver can be evaluated by the measuring means using resonance measuring in the frequency range between 0 and 10 kHz.

In a development of the invention, it is provided that the probe has a guiding member fixable to the surface structure to be examined, in which guiding member the probe is guided orthogonal to the surface structure and in which the probe can assume different defined angular positions using marks at he probe and at the guiding member. The guiding member, which may be a cylindrical sleeve, for example, glued to the surface structure to be examined, receives the probe such that an orthogonal orientation of the probe relative to the surface structure is ensured. Moreover, the circumference of the guiding member is provided with angular marks that, together with a mark on the probe, allow to rotate the probe through predetermined angles so that measurements can be made under an angle of 0°, 45°, 90°, or 135°, for example, relative to an initial position.

BRIEF DESCRIPTION OF THE DRAWING

The following is a detailed description of an embodiment of the present invention with reference to the accompanying drawing.

In the Figures.

DETAILED DESCRIPTION OF A PREFERRED EMBODIMENT

Figure 1:
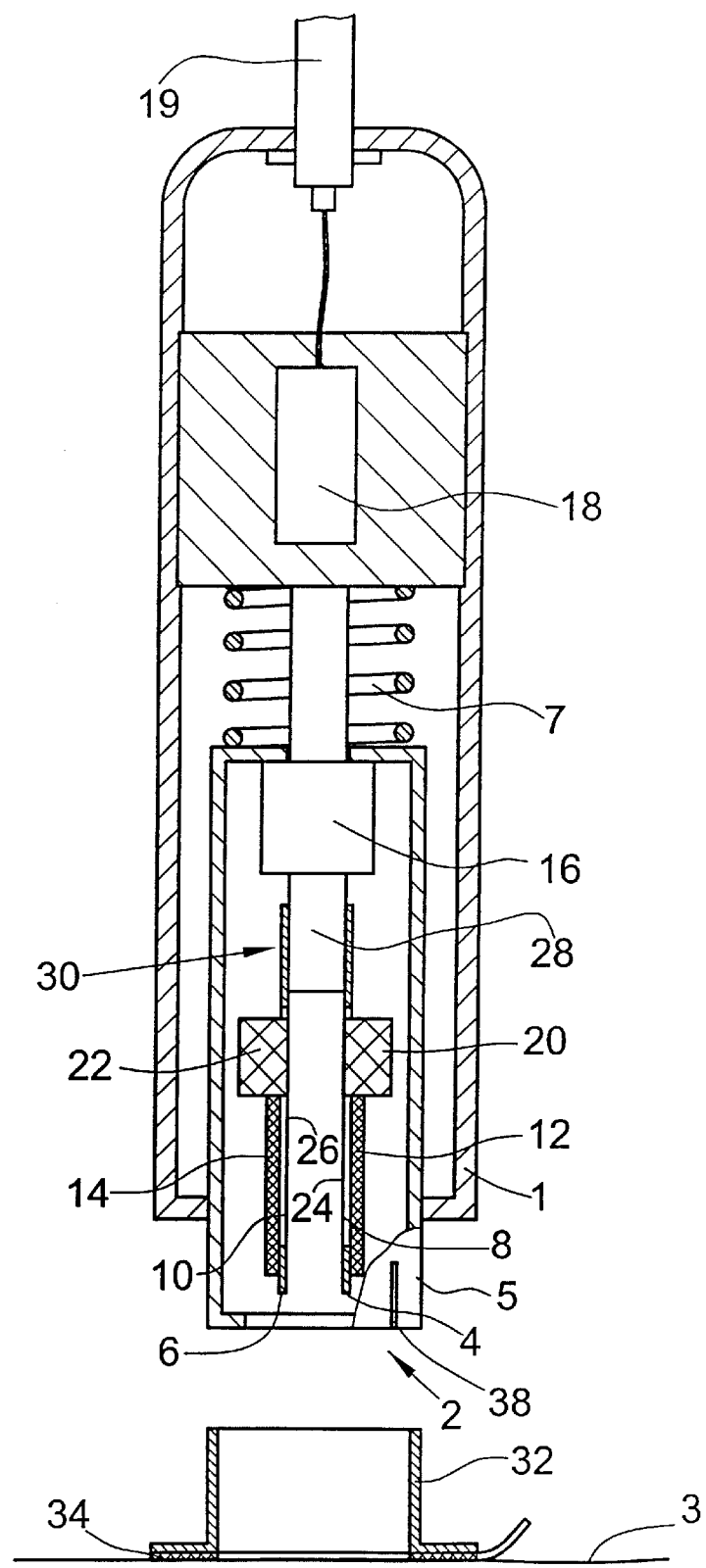
FIG. 1 illustrates a cross-section through the measuring device.

The measuring device illustrated in FIG. 1 comprises a housing 1, wherein a probe 2 is axially movable. The probe 2 consists of a housing 5 in which a support 28 is provided to which two flat strip-shaped longitudinally extending holders 8, 10 are fastened spaced parallel from each other, each holder receiving a bi-morph element 12, 14. The holders 8, 10 are made of Makrolon and have a high flexibility. Only one side of the holders 8, 10 fastened to the support 28 and can vibrate freely with their free ends.

The free ends of the holders 8, 10 at the same time form the measuring tips 4, 6 through which vibrations of an acoustic pulse from a bi-morph element are transmitted to the surface structure 3 to be examined. The bi-morph element 12 extends in strip-shape parallel to the holder 8 and, in the area of the measuring tip 4, it is preferably glued on the outer side. The free end of the bi-morph element 12 averted from the measuring tip 4 carries a seismic mass 20, preferably glued on.

Figure 2:
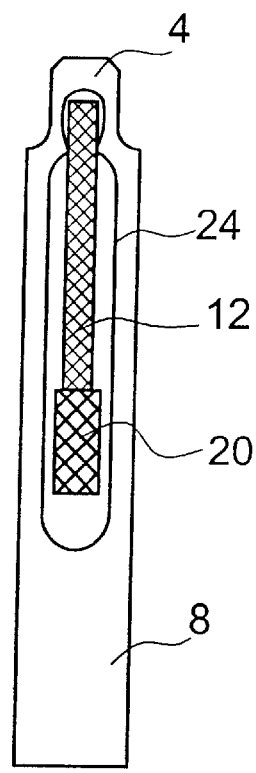
FIG. 2 is a top plan view on a holder with a bi-morph element.

An electric pulse provided to the bi-morph element 12 by a control means 16 with a power electronics generates a bending moment in the bi-morph element and transmits an acoustic pulse to the measuring tip 4. The seismic mass 20 serves to counter the moment. The inertia of the mass 20 causes the arrangement to be very sensitive to fast pulses, yet hardly sensitive to relatively slow movements caused by improper handling with the device. The bi-morph element 12 forms a transmitter for acoustic pulses together with the measuring tip 4 and the seismic mass 20. Mirrored about the longitudinal axis of the measuring device through the support 28, there is a receiver formed by the measuring tip 6, the holder 10, the bi-morph element 14 and the seismic mass 22. As is best illustrated in FIG. 2, the holders 8, 10 have a recess 24, 26 that allow for a free vibration of the bi-morph elements 12, 14 and the seismic masses 20, 22 in a direction orthogonal to the holders 8, 10.

The housing 5 and the measuring probe 2 are biased within the housing 1 using a pressure spring 7.

An evaluating means 18 analyzes the measuring signals picked up by the measuring tip 6 through resonance measuring in a frequency range from 0 to 10 kHz, for example.

The results of the measurements may be displayed on the display of a display means not illustrated that is connected to the evaluating means 18 through a wire 19.

A hollow cylindrical guiding means 32 can accommodate the distal end of the probe 2 so that the measuring tips 4, 6 are orientated exactly orthogonal to the skin surface 3 during measurement. The guiding element 32 has a flange with a substantially annular double-sided adhesive film 34 on the side facing the surface structure 3. Using the double-sided adhesive film 34, the guiding member 32 can be fixed at a site of the surface structure 3 to be examined.

Figure 3:
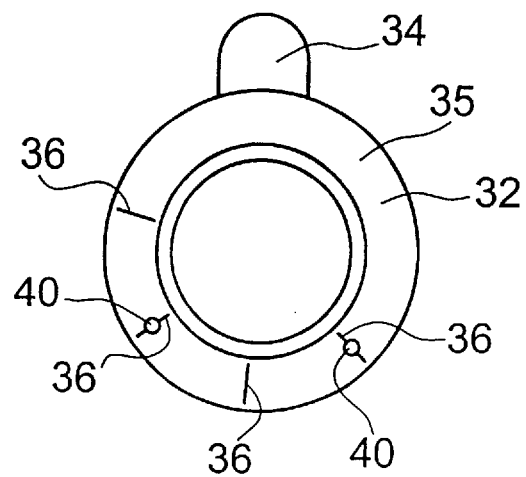
FIG. 3 is a top plan view on a guiding member for the probe.

As is best seen in FIG. 3, the annular flange 35 has two holes 40 provided in the circumference, serving to apply color marks on the surface structure 3, e.g. with a pen, so as to be able to perform the measurement at the same site under the same orientation of the probe 2 also in larger time intervals.

It should be noted that it is essential to the value of the measuring results that the measuring results to be compared are taken from the same site of the surface structure 3.

Further, the annular flange has marks 36 that have a predetermined angular distance from each other. In connection with a mark 38 on the exterior of the housing 1 of the probe 2 (FIG. 1), the measuring device can be positioned reproducibly on the same measuring site and in the same angular position on the surface structure 3.

The display means can then be used to display measured values, e.g. under an angle of 0°, 45°, 90° and 135°, so that statements on the anisotropy surface structure 3 may also be made.

It is further possible to display average values of repeated measurements on the display means. The evaluating means 18 is also able to store measured values for later comparison.

The measurement can be triggered by pressing the measuring tips 4, 6 against the skin surface 3 using a certain bias. The amount of bias may for example be determined through measurement of the probe path which measures the axial displacement of the probe 2 against the spring force. In addition, the triggering of the acoustic pulse and the measuring can be delayed in time.

The acoustic pulses used lie in the range between 0.5 and 30 kHz.

The measured values are representative for the elastic properties of the surface structure for which also different elasticity values for the transverse and longitudinal elasticity can be determined.

The surface structure 3 may consist of elastic vibratory materials whose viscoelastic properties can be examined. The measuring device is also applicable in material tests for different materials or in production control, for example, for rubber- or leather-like materials.

An important field of application of such measurements in the dermatological field is the measurement of the viscoelasticity and anisotropy of the skin, e.g. for examining the effects of cosmetics and pharmaceuticals on collagen and elastin fibers in the skin, mammographic tests, and tests in connection with the treatment of scars.

What is claimed is:

1. A measuring device for measuring the elastic properties of a surface structure comprising a probe (2) arranged within a housing (5), a transmitter (4, 8, 12, 20) and at least one receiver (6, 10, 14, 22), the transmitter being adapted to transmit acoustic pulses and the receiver being adapted to pick up the propagation behavior of the acoustic pulse in the surface structure, control means (16) for generating acoustic pulses, evaluting means (18) for measuring signals received by the receiver, at least two holders (8, 10) each are connected as measuring tip (4, 6, respectively) which are connected as transmitting and receiving elements and being adapted to seat upon a surface structure for measuring the elastic properties thereof, a strip-shaped bi-morph element (12, 14) carried by each holder (8, 10), each measuring tip (4, 6) being an integral portion of an associated holder (8, 10), the strip-shaped bi-morph element (12, 14) each having an end most adjacent an associated measuring tip (4, 6) fastened to the associated holder (8, 10), a seismic mass (20, 22) fastened at a free end of each strip-shaped bi-morph element (12, 14) remote from the associated measuring tip (4, 6, respectively), and the holders (8, 10) having ends remote from the tips (4, 6, respectively) fastened to a support (28) of the probe (2).

2. The measuring device as defined in claim 1 wherein the holders (8, 10) each have an elongated recess (24, 28, respectively) within which the bi-morph elements (12, 14 respectively) are free to vibrate.

3. The measuring device as defined in claim 1 wherein the holders (8, 10) are each a flat strip of material.

4. The measuring device as defined in claim 1 wherein the probe (12) is supported for axial movement in the housing (5), and spring means (7) for biasing the measuring tips (4, 6) against the surface structure undergoing measurement.

5. The measuring device as defined in claim 4 wherein the control means (16) triggers the acoustic pulse and measurement after the probe (2) has traveled as predetermined path.

6. The measuring device as defined in claim 5 wherein the control means (16) triggers the acoustic pulse and the measurement after a predetermined time delay.

7. The measuring device as defined in claim 1 wherein the evaluating means (18) includes resonance measuring means in the frequency range from 0 to 10 khz to evaluate the signals picked up by the receivers (6, 10, 14, 22).

8. A measuring device for measuring the elastic properties of a surface structure comprising a probe (2) arranged within a housing (5), a transmitter (4, 8, 12, 20) and at least one receiver (6, 10, 14, 22), the transmitter being adapted to transmit acoustic pulses and the receiver being adapted to pick up the propagation behavior of the acoustic pulses in the surface structure, control means (16) for generating acoustic pulses, evaluating means (18) for measuring signals received by the receiver, at least two holders (8, 10) each including a respective measuring tip (4, 6 respectively) which are connected as transmitting and receiving elements and being adapted to seat upon a surface structure for measuring the elastic properties thereof, a strip-shaped bi-morph element (12, 14) carried by each holder (8, 10), each measuring tip (4, 6) being an integral portion of an associated holder (8, 10), the strip-shaped bi-morph elements (12, 14) each having an end most adjacent an associated measuring tip (4, 6) fastened to the associated holder (8, 10), the phone (2) includes guide means (32) adapted to be secured to the surface structure under measurement, and the probe (2) and guide means (32) include cooperative marking means (38; 36, 40) for effecting different angular positions therebetween.

9. The measuring deice as defined in claim 1 wherein the holders (8, 10) each have an elongated recess (24, 28, respectively) within which the bi-morph elements (12, 14, respectively) are housed.

10. The measuring device as defined in claim 9 wherein the holders (8, 10) are each a flat strip of material.

11. The measuring device as defined in claim 9 wherein the probe (12) is supported for axial movement in the housing (5), and spring means (7) for biasing the measuring tips (4, 6) against the surface structure undergoing measurement.

12. The measuring device as defined in claim 10 wherein the probe (12) is supported for axial movement in the housing (5), and spring means (7) for biasing the measuring tips (4, 6) against the surface structure undergoing measurement.

* * * * *